(12) United States Patent
Granz et al.

(10) Patent No.: US 9,675,253 B2
(45) Date of Patent: Jun. 13, 2017

(54) ANIMAL HANDLING ARRANGEMENT AND METHOD

(75) Inventors: Susanne Granz, Grodinge (SE);
Kendra Kerrisk, New South Wales (SE); Bohao Liao, Sollentuna (SE);
Ron Mulder, TeAroha (NZ)

(73) Assignee: DELAVAL HOLDING AB, Tumba (SE)

( * ) Notice: Subject to any disclaimer, the term of this patent is extended or adjusted under 35 U.S.C. 154(b) by 920 days.

(21) Appl. No.: 14/007,508

(22) PCT Filed: Apr. 4, 2012

(86) PCT No.: PCT/SE2012/050370
§ 371 (c)(1),
(2), (4) Date: Nov. 29, 2013

(87) PCT Pub. No.: WO2012/138290
PCT Pub. Date: Oct. 11, 2012

(65) Prior Publication Data
US 2014/0180130 A1    Jun. 26, 2014

Related U.S. Application Data

(60) Provisional application No. 61/471,810, filed on Apr. 5, 2011.

(30) Foreign Application Priority Data

Apr. 5, 2011   (SE) .................................... 1150295-2

(51) Int. Cl.
*A61D 99/00*   (2006.01)
*A61B 5/00*   (2006.01)
(Continued)

(52) U.S. Cl.
CPC ............ *A61B 5/0073* (2013.01); *A01K 29/00* (2013.01); *A61B 5/1077* (2013.01);
(Continued)

(58) Field of Classification Search
CPC .... A61D 99/00; A01K 29/005; A61B 5/0073; A61B 5/4238
See application file for complete search history.

(56) References Cited

U.S. PATENT DOCUMENTS 4,745,472 A   5/1988   Hayes
5,412,420 A   5/1995   Ellis
(Continued)

FOREIGN PATENT DOCUMENTS

EP   1 900 278 A1   3/2008
RU   2106081 C1   3/1998
(Continued)

OTHER PUBLICATIONS

Supplementary International Search Report, dated Jul. 12, 2013, from corresponding PCT application.
(Continued)

*Primary Examiner* — Alyssa M Alter
(74) *Attorney, Agent, or Firm* — Young & Thompson

(57) ABSTRACT

A method and arrangement for determining a gut fill level of the rumen of an animal uses a three-dimensional camera and an image processing system. The three-dimensional camera is located in a station, wherein the animal is forced to stand essentially still during recording of the three-dimensional image. The three-dimensional camera is located on the left side of the animal at a height above the rumen triangle of the animal, longitudinally in essence in level with the rumen triangle, and is directed downwards towards the rumen triangle during the image recording. The image processing system automatically determines a depth and/or volume of a
(Continued)

convexity or concavity of the rumen triangle, and determines the gut fill level of the rumen of the animal based on the determined depth and/or volume.

20 Claims, 1 Drawing Sheet

(51) Int. Cl.
*A01K 29/00* (2006.01)
*A61B 5/107* (2006.01)
(52) U.S. Cl.
CPC .......... *A61B 5/1079* (2013.01); *A61B 5/4238* (2013.01); *A61D 99/00* (2013.01)

(56) References Cited

U.S. PATENT DOCUMENTS

| 2003/0024481 | A1 | 2/2003 | Kalscheur et al. |
| 2004/0023612 | A1 | 2/2004 | Kriesel |
| 2004/0032974 | A1 | 2/2004 | Kriesel |
| 2005/0011466 | A1 | 1/2005 | Doyle, II |
| 2006/0126903 | A1 | 6/2006 | Sharony |
| 2008/0273760 | A1 | 11/2008 | Metcalfe et al. |
| 2010/0154722 | A1 | 6/2010 | Van Den Berg et al. |
| 2010/0289879 | A1 | 11/2010 | Sinzinger et al. |

FOREIGN PATENT DOCUMENTS

| RU | 2322048 C2 | 4/2008 |
| SU | 1037896 A1 | 8/1983 |
| SU | 1309936 A2 | 5/1987 |
| SU | 1727741 A1 | 4/1992 |
| WO | 01/67039 A1 | 9/2001 |
| WO | 2004/012146 A1 | 2/2004 |
| WO | 2009/028930 A1 | 3/2009 |
| WO | 2010/063527 A1 | 6/2010 |
| WO | 2010127023 A1 | 11/2010 |

OTHER PUBLICATIONS

International Search Report, dated Jul. 12, 2012, from corresponding PCT application.
International Type Search Report, dated Nov. 17, 2011, from corresponding 1150295-2.

ANIMAL HANDLING ARRANGEMENT AND METHOD

TECHNICAL FIELD OF THE INVENTION

The present invention relates generally to animal farming, and particularly to arrangements and methods including approaches for automatically determining gut fill levels of rumens of animals.

DESCRIPTION OF RELATED ART AND BACKGROUND OF THE INVENTION

By weighing animals daily or twice daily, body weight trends can be obtained. From these trends it can be deduced whether an animal or a group of animals loses or gains body weight over a number of days. However, body weight trends have less importance for herd management as the body weight can change due to changes in body fat, frame size, gut size, udder size, pregnancy status, and intake of food and water.

Body condition scoring is a method of evaluating fatness or thinness in cows according to a scale, e.g. a five-point scale, where a score of one denotes a very thin cow, while five denotes an excessively fat cow. Research and field experiments have shown that body condition influences productivity, re-production, health and longevity. Thus, thinness or fatness can indicate underlying nutritional deficiencies, health problems, or improper herd management. As a mean to detect problems within the herd, body condition scoring is a good aid in improving the health and productivity of a dairy herd, when done on a regular basis, thus acting as an efficient tool in good herd management.

Determining gut fill levels of the rumens of animals can also assist in the herd management. US 2010/0154722 A1 relates to a system for managing a group of animals, and discloses a 2D/3D camera arranged straight behind or obliquely to the left behind a cow to observe a part of the cow. In one embodiment, the 2D/3D camera forms a depth-image of the left side, on the basis of which a central processing unit determines a score which is representative of a content of the paunch. On the basis of the score for the paunch contents of the cow in question, the central processing unit subsequently generates control information which is related to the feed intake of the cow in question on the relevant day. At a low score, which means that the cow has eaten little to nothing, the control information comprises a signal for a user that the cow in question should be separated because of possible illness, is not allowed to have access to feed, and/or is on heat.

SUMMARY OF THE INVENTION

The present inventors have noted a few shortcomings with the known approach for automatic gut fill level determination as disclosed in US 2010/0154722 A1.

Firstly, US 2010/0154722 A1 fails to disclose how the score which is representative of a content of the paunch is determined. In paragraph [0036] general image processing is disclosed, but no method whatsoever is disclosed which shows how the above score can be determined. As a result, US 2010/0154722 A1 seems to fail to provide an enabling disclosure on how the score which is representative of a content of the paunch is actually determined.

Secondly, by arranging the camera behind the animal still more difficulties may be obtained since for some animals the image angle does not allow the entire paunch to be imaged. This is particularly troublesome for animals with low gut fill level wherein the paunch is a concavity, sometimes a deep concavity.

Thirdly, imaging the paunch of the animal when the animal is in a shed or a pasture is difficult since the animal typically moves around. It may be difficult to at all record an image of the paunch of the animal, and if an image of the paunch is recorded, motion blur may reduce the spatial resolution in the image, and render any information deduced from the image unreliable and imprecise.

Accordingly, it is an object of the present invention to provide an arrangement and method for animal handling, which determines gut fill levels of rumens of animals in a manner which alleviates the shortcomings of the prior art.

It is a further object of the invention to provide such arrangement and method, which are automated, robust, effective, fast, precise, accurate, reliable, safe, easy to use, and of reasonable cost.

These objects among others are, according to the present invention, attained by arrangements and methods as claimed in the appended patent claims.

According to one aspect of the invention an animal handling arrangement is provided, the animal handling arrangement comprising a herd management system and an arrangement for determining a gut fill level of the rumen of an animal, which comprises a three-dimensional camera arranged to be directed towards the animal for recording at least one three-dimensional image of the animal or portion thereof, and an image processing system connected to the three-dimensional camera for automatically analyzing the three-dimensional image and determining the gut fill level of the rumen of the animal based on the analyzed three-dimensional image. The animal handling arrangement is arranged to automatically supply the herd management system with the determined gut fill level of the rumen of the animal and the herd management system is arranged to automatically initiate an animal related action based on the determined gut fill level. According to the invention the three-dimensional camera is located in a station, wherein the animal is forced to essentially stand still during the recording of the at least one three-dimensional image of the animal or portion thereof; the three-dimensional camera is located on the left side of the animal at a height above the rumen triangle of the animal, and longitudinally in essence in level with the rumen triangle of the animal, and is directed downwards towards the rumen triangle of the animal in the station during the image recording to give image information from there; and the image processing system is arranged to automatically determine a depth and/or volume of a convexity or concavity of the rumen triangle, and to determine the gut fill level of the rumen of the animal based on the determined depth and/or volume of the convexity or concavity of the rumen triangle. Preferably, the station is any of a waiting station, a feeding station, a treating station, or a milking station.

Hereby, reliable automatic determination of gut fill levels of rumens of animals is achieved with high accuracy and precision, on which animal handling can be based.

It shall be appreciated that by the expression longitudinally in essence in level with the rumen triangle of the animal means that the three-dimensional camera should be directed with its optical axes in essence perpendicular to the longitudinal axis of the animal. However, a deviation of up to about 10-15 degrees from the perpendicular direction would normally be acceptable. The importance is that the bottom of the rumen triangle concavity should advantageously be clearly visible from the camera position for a large variety of animals, such that the depth and/or volume of the rumen triangle concavity can be reliably calculated in accordance with the invention. The inventors have noted that if the three-dimensional camera is not located longitudinally as disclosed above, sometimes the bottom of the rumen triangle concavity is not visible from the camera position, and as a result, the determined gut fill level of the rumen of the animal is not reliable.

Similarly, in the vertical direction, the three-dimensional camera should be located above the level of the rumen triangle and be directed slightly downwards in such a way that the bottom of a rumen triangle concavity is advantageously clearly visible from the camera position for a large variety of animals, such that the depth and/or volume of the rumen triangle concavity can be reliably calculated. The inventors have noted that if the three-dimensional camera is not located vertically above the level of the rumen triangle, sometimes the bottom of the rumen triangle concavity is not visible from the camera position and as a result, the determined gut fill level of the rumen of the animal is not reliable.

Preferably, the three-dimensional camera is directed downwards towards the rumen triangle of the animal with an angle between the optical axes of the three-dimensional camera and the horizontal plane of between about 25 and about 75 degrees, since this means that the camera is directed almost tangentially towards the rumen triangle of the animal.

The three-dimensional camera may be a time of flight range camera or an active wave front sampling camera which provides a two-dimensional image of the animal, wherein, for each pixel of the two-dimensional image, the distance between the three-dimensional camera and the respective object point imaged is provided.

According to a further aspect of the invention a method for determining a gut fill level of the rumen of an animal is provided. According to the method, a three-dimensional camera is directed from a position located on the left side of an animal at a height above the rumen triangle of the animal, and longitudinally in essence in level with the rumen triangle of the animal towards the rumen triangle of the animal when the animal is located in a station, in which the animal is forced to essentially stand still, while at least one three-dimensional image of the rumen triangle of the animal is recorded. The three-dimensional image is automatically analyzed, wherein a depth and/or volume of a convexity or concavity of the rumen triangle is automatically determined. The gut fill level of the rumen of the animal is automatically determined based on the determined depth and/or volume of the convexity or concavity of the rumen triangle. Finally, the determined gut fill level is automatically forwarded to a herd management system and an animal related action is automatically initiated based on the determined gut fill level.

Various embodiments of the invention are set out in the dependent claims.

The present inventors have noted that the depth and volume of the rumen triangle concavity vary depending on the size of the animal for a given gut fill level of the rumen. Therefore, various embodiments are suggested which minimize the effect of the size of the animal on the determined gut fill level.

In one embodiment, the depth of the convexity or concavity of the rumen triangle of the animal is normalized with respect to the size of the animal, wherein the size of the animal is given as a length of the animal, a height of the animal, a width of the animal, a volume of the animal, a weight of the animal, or a combination thereof.

In another embodiment, the volume of the convexity or concavity of the rumen triangle of the animal normalized with respect to the size of the animal, wherein the size of the animal is given as indicated above.

In yet another embodiment, the difference from time to time of the depth and/or volume of the convexity or concavity of the rumen triangle of the animal is used as an indicator of a relative gut fill level of the rumen of the animal. For instance, a previous depth and/or volume of the convexity or concavity of the rumen triangle of the animal, e.g. based on a previous recording of a three-dimensional image of the rumen triangle of the animal, is compared to the currently determined depth and/or volume of the convexity or concavity of the rumen triangle, and the gut fill level of the rumen of the animal is determined based on the comparison. For instance, the difference between the previous depth and/or volume of the convexity or concavity of the rumen triangle and the currently determined depth and/or volume of the convexity or concavity of the rumen triangle may be used as the indicator, optionally divided by the previous depth and/or volume of the convexity or concavity of the rumen triangle to obtain a percentage deviation. The previous depth and/or volume of the convexity or concavity of the rumen triangle of the animal may be a depth and/or volume, such as e.g. a mean value of the depth and/or volume for measurements performed during a period of time, or it may be a depth and/or volume determined and correlated with a gut fill level determined by other means, e.g. manually.

In the simplest algorithm, the gut fill level of the rumen of an animal may be determined as the depth or volume of the convexity or concavity of the rumen triangle, optionally after normalization according to the above.

Alternatively, the gut fill level of the rumen of an animal may be determined as a sum, optionally weighted, or a product of the depth and the volume of the convexity or concavity of the rumen triangle, optionally after normalization according to the above.

Yet alternatively, the gut fill level of an animal may be determined as a percentage change of the depth or volume of the convexity or concavity of the rumen triangle of an animal. The percentage change may relate to the change since the last measurement being performed, or it may relate to a change with respect to a depth or volume of the convexity or concavity of the rumen triangle of the animal for a known gut fill level.

In a further embodiment, the gut fill level of the rumen of the animal is determined based also on a model which links results of image analysis of three-dimensional images of animals, or portions thereof, to independently measured depths of the convexity or concavity of the rumen triangle of the animals, and gut fill levels manually determined by experts.

In yet a further embodiment, if the measured gut fill level of the rumen of an animal deviates from the expected gut fill level by at least a given amount, this triggers an alarm to be activated or an action to be taken automatically with respect to the animal, e.g. the animal could be treated in some manner, by means of an animal treatment system or the animal could be fed with feed changed with respect e.g. to its nutritional content.

The gut fill level of the rumen is a direct measurement of the fillingness of the rumen, which is related directly to the feed-intake and water intake of a cow. It gives a fast response to abnormal feed intake due to for instance diseases or bad quality of feed compared with body weight or body condition conditioning. Therefore it is a more efficient indication of feed intake disturbances.

For instance, the determination of the gut fill level of the rumen of an animal can be used in automatic identification of bloat, a lethal condition for cows. Typically, if a cow is bloated, the rumen will be bulging slightly and feel distended and tight like a balloon. This condition is very serious and the animal may be likely to die if it is not treated directly. Thus, if bloat is detected an alarm will be initiated directly and in some instances an automatic treatment is initiated without delay, e.g. applying a troche to release air pressure from the rumen. This aspect of the invention is of high importance and would be a significant tool in animal management to maintain good animal health.

Further, if the animal is on pasture, the herd management system may comprise means for determining the number of grazing hours left in a paddock based on the established feed consumption of the animal, which in turn is based on the determined gut fill level. If this is done for all animals in the paddock, the total number of grazing hours left in the paddock can be calculated from the amount of grass in the paddock at start and the feed consumed in the paddock (as determined from the determined gut fill levels). This, in turn, may be used for the planning and control of the animal traffic between different paddocks.

If the animal is a milking animal, the gut fill level, or feed consumption estimated from there, may be used in the control of animal traffic in the milking system.

Advantages of the invention as compared to the usually conducted and manually performed gut fill assessment by experienced herdsman via visual inspection and contact include the following:

The automatically performed gut fill assessment of the invention is not subjective; it is not influenced by environment such as lighting, impression, knowing of animals, or personally dependent.

Further, it is cost efficient and no time consuming work by skilled herdsman is required. The invention can easily be employed in large herds with high number of animals on a daily basis. The gut fill levels can thus be traced and tracked frequently.

Advantages of the invention as compared to both the usually conducted and manually performed gut fill assessment by experienced herdsman and the approach disclosed in US 2010/0154722 A1 include the following:

The reliability, accuracy and precision of the gut fill assessment are increased.

Further, the resolution of the gut fill assessment is increased.

The determined gut fill level can be used in e.g. detecting bloat, in milking permission decisions, in decisions for feed assignment changes, and in estimating grazing hours left in pasture grazing planning.

Further characteristics of the invention and advantages thereof, will be evident from the following detailed description of preferred embodiments of the present invention given hereinafter and the accompanying FIGS. 1-3, which are given by way of illustration only, and are thus not limitative of the present invention.

DETAILED DESCRIPTION OF EMBODIMENTS

Figure 1A:
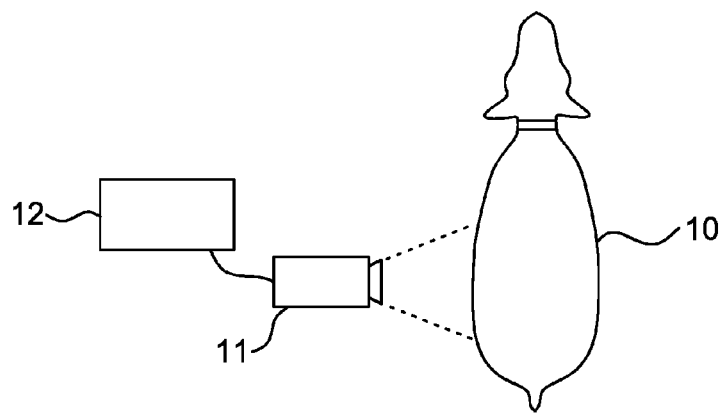
FIG. 1a illustrates schematically an arrangement for determining a gut fill level of the rumen of an animal according to an embodiment of the present invention.
Figure 1B:
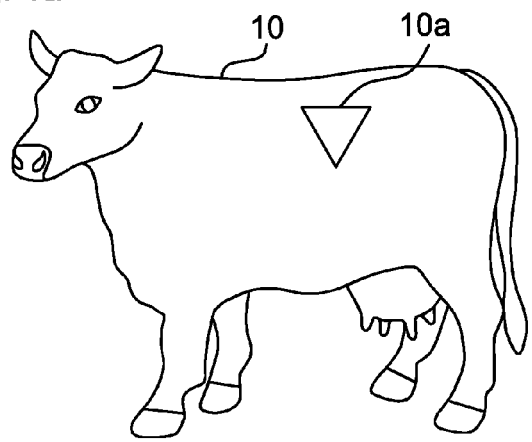
FIG. 1b illustrates schematically the so-called rumen triangle of an animal.

FIG. 1a shows an arrangement for determining a gut fill level of the rumen of an animal such as a cow 10 comprising a three-dimensional camera 11 directed towards the cow 10 and arranged to instantaneously record at least one three-dimensional image of the cow 10 or portion thereof, and an image processing system 12, such as a microcomputer provided with suitable software, connected to the three-dimensional camera 11.

The image processing system 12 is arranged to process the three-dimensional image recorded by the three-dimensional camera 11 and for determining the gut fill level of the rumen of the cow 10 based on the processed three-dimensional image.

The three-dimensional camera 11 is preferably time of flight range camera such as the Mesa Imaging AG® Swiss Ranger SR-3000 sensor. This is a complete solid-state Time-of-Flight range camera developed by CSEM (Centre Suisse d'electronique et de microtechnique). It is connected to the microcomputer 12 via USB 2.0 for direct measurement of real-time depth maps and is designed for operation under indoor lighting conditions.

The time of flight (TOF) technique is based on measurements of the distance to an object based on the time that it takes for the infra red light with a peak wavelength of 850 nm to reflect on the object and reach the sensor while traveling at a known speed. The measured distance is proportional to twice the time needed for the waves to travel from the camera to the object. What is actually measured is a phase shift between the outgoing signal and the detected reflected signal.

The above exemplified camera is based on a two dimensional image sensor with a field of view of 47.5×39.6 degrees with a spatial resolution of 176×144 pixels using a CMOS active-pixel sensor. The technology is very similar to CCD-technology. The resulting output is a four dimensional representation of the view showing the intensity information at each pixel, in correlation with an ordinary digital camera. In addition, each point's relative position to the camera is given with its x, y and depth (z) value. When combining the information in the x-, y- and z-channels, it is possible to create a three-dimensional visualization of the scene.

Setting the amplitude threshold, noisy pixels can be filtered. The amplitude determines the amount of emitted light that is reflected back on the pixel. The integration time controls the exposure time for the acquired image.

Alternatively, the three-dimensional camera 11 is based on another technology to provide the three-dimensional visualization of the scene. For instance, the three-dimensional camera 11 may be a camera using laser triangulation or a stereo vision system, optionally equipped with a light source and speckle generating arrangement for creating light having a speckle pattern. Yet alternatively, the three-dimensional camera 11 is an active wave front sampling camera, which has a two-dimensional array of pixels and which is capable of providing, for each of the pixels, a distance between the camera and the object point imaged.

Virtually any kind of three-dimensional camera that is capable of providing three-dimensional surface representations of the scene may be used in the present invention.

The three-dimensional camera 11 is located on the left side of the cow 10 at a height above the so-called rumen triangle 10a of the cow 10, and longitudinally in essence in level with the rumen triangle 10a of the cow 10, and is directed downwards towards the rumen triangle 10a of the cow 10 during the image recording to give image information from there. The rumen triangle 10a may also be referred to as the paralumbar fossa.

By the expression longitudinally in essence in level with the rumen triangle 10a of the cow 10 means that the three-dimensional camera should be directed with its optical axes in essence perpendicular to the longitudinal axis of the animal. However, a deviation of up to about 10-15 degrees from the perpendicular direction would normally be acceptable. It is of significance that the bottom of a rumen triangle concavity should be clearly visible from the camera position for a large variety of cows, such that the depth and/or volume of the rumen triangle concavity can be reliably calculated.

Similarly, in the vertical direction, the three-dimensional camera 11 should be located above the level of the rumen triangle 10a and be directed slightly downwards in such a way that the bottom of a rumen triangle concavity is advantageously clearly visible from the camera position for a large variety of cows. Preferably, the three-dimensional camera 11 is directed downwards towards the rumen triangle 10a of the cow 10 with an angle between the optical axes of the three-dimensional camera 11 and the horizontal plane of between about 25 and about 75 degrees, since this means that the camera is directed almost tangentially towards the rumen triangle of the animal.

The three-dimensional image has typically at least 160× 120 pixels and provides position (x, y, and z) values as well as an intensity value for each of the pixels. Preferably double exposures are used with different integration time to handle the contrast depth from white to black (some cows are very light in color, whereas other are dark in color). The images with short and long integration times of each cow 10 are merged to form a single image of high dynamic range and quality.

Next pre-processing of the image data, including filtering, outliner removal, and cow body extraction, may be performed. Thereafter, parameter extraction may be performed. The tail and hip bones are then identified in the image.

Preferably, the image processing system 12 is arranged to automatically analyze the convexity or concavity of the rumen triangle 10a in the three-dimensional image, and to determine the gut fill level of the rumen 10a of the cow 10 based on the analyzed convexity or concavity of the rumen triangle 10a. In particular, the image processing system 12 may be arranged to automatically determine a depth of the convexity or concavity of the rumen triangle 10a, and to determine the gut fill level of the rumen of the cow 10 based on the determined depth of the convexity or concavity of the rumen triangle 10a.

Alternatively, or additionally, the image processing system 12 may be arranged to automatically determine the volume of the convexity or concavity of the rumen triangle 10a, and to determine the gut fill level of the rumen of the cow 10 based on the determined volume of the convexity or concavity of the rumen triangle 10a.

The depth and/or the volume of the convexity or concavity of the rumen triangle 10a can be normalized with respect to the size of the cow 10, wherein the size of the cow 10 is given as a length of the cow, a height of the cow, a width of the cow, a volume of the cow, a weight of the cow, or a combination thereof.

The length and height of the cow 10 can be measured from an image covering the whole length and height of the cow 10 as measured by the three-dimensional camera 11, or by any other measurement device. Similarly, the width and the volume of the cow 10 may be measured and estimated from images taken of the cow 10 by a camera arrangement operatively connected to the image processing system 12. The weight of the cow 10 may be measured by a weighing device, which is operatively connected to the image processing system 12. The length of the cow, the height of the cow, the width of the cow, the volume of the cow, the weight of the cow, and a combination thereof may be determined in any manner known in the art and forwarded to the image processing system 12 for normalization purposes.

In another embodiment, the difference from time to time of the depth and/or volume of the convexity or concavity of the rumen triangle of the cow 10 is used as an indicator of a relative gut fill level of the rumen of the animal. For instance, a previous depth and/or volume of the convexity or concavity of the rumen triangle 10a of the cow 10, e.g. based on a previous recording of a three-dimensional image of the rumen triangle 10a of the cow 10, is compared to the currently determined depth and/or volume of the convexity or concavity of the rumen triangle 10a, and the gut fill level of the rumen of the cow 10 is determined based on the comparison. For instance, the difference between the previous depth and/or volume of the convexity or concavity of the rumen triangle 10a and the currently determined depth and/or volume of the convexity or concavity of the rumen triangle 10a is used as the indicator, optionally divided by the previous depth and/or volume of the convexity or concavity of the rumen triangle 10a to obtain a percentage deviation.

In one algorithm, the gut fill level of the rumen of a cow 10 may be determined as the depth or volume of the convexity or concavity of the rumen triangle, optionally after normalization according to the above.

Alternatively, the gut fill level of the rumen of a cow 10 may be determined as a sum, optionally weighted, or a product of the depth and the volume of the convexity or concavity of the rumen triangle 10a, optionally after normalization according to the above.

Yet alternatively, the gut fill level of an animal may be determined as a percentage change of the depth or volume of the convexity or concavity of the rumen triangle 10a of the cow 10.

Further, the gut fill level of the rumen of the cow 10 may be determined based also on the breed of the cow 10, the pregnancy status of the cow 10, and optionally a body condition score of the cow 10.

Yet further, the gut fill level of the rumen of the cow 10 may be determined based also on the composition, particle size, structure, digestibility, and/or fiber content of feed last consumed by the cow 10, the time lapsed since feed was last consumed by the cow 10, and/or the amount of feed last consumed by the cow 10.

It shall here be stressed that the gut fill level of the rumen of a cow 10 is a result of dry matter intake, ration composition, digestion, and the passage rate of ingested food. The digestibility of a feed ration is the result of the feed retention time in the rumen and the degradation characteristics of ingested nutrients (particle sixe, type of fibers, etc.). The more fibers that are ingested, the lower is the digestibility and the longer is the passage rate. This has to be taken into consideration when determining the gut fill level of the rumen of the cow 10.

In any of the embodiments disclosed above, the gut fill level of the rumen of the cow 10 can be determined based on a model which links results of image analysis of three-dimensional images of cows, or portions thereof, to independently measured depths of the convexity or concavity of the rumen triangle of the cows, and/or gut fill levels manually determined by experts. Such model may be dynamically modified in order to better and better determine gut fill levels. It may be based on an artificial neural network. The determined gut fill levels may be given as a positive integer from one to five.

Figure 2:
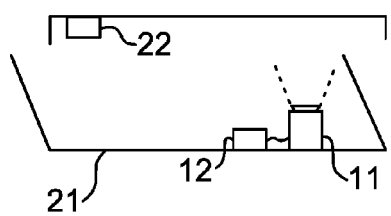
FIG. 2 illustrates schematically an animal arrangement including a feeding, milking, or resting station according to an embodiment of the invention.

The inventive arrangement is arranged in a cow arrangement such as a waiting, treating, feeding, milking, or resting station provided preferably with a cow identification device, wherein the cow 10 is forced to essentially stand still during the recording of the at least one three-dimensional image of the cow 10 or portion thereof. Such embodiment is illustrated in FIG. 2 where the waiting, treating, feeding, milking, or resting station is denoted by 21 and the cow identification device is denoted by 22.

Preferably, the inventive arrangement is arranged to determine the gut fill level of the rumen of each cow repeatedly at a rather high frequency such as e.g. daily or several times a day, e.g. each time the cow is milked.

Figure 3:
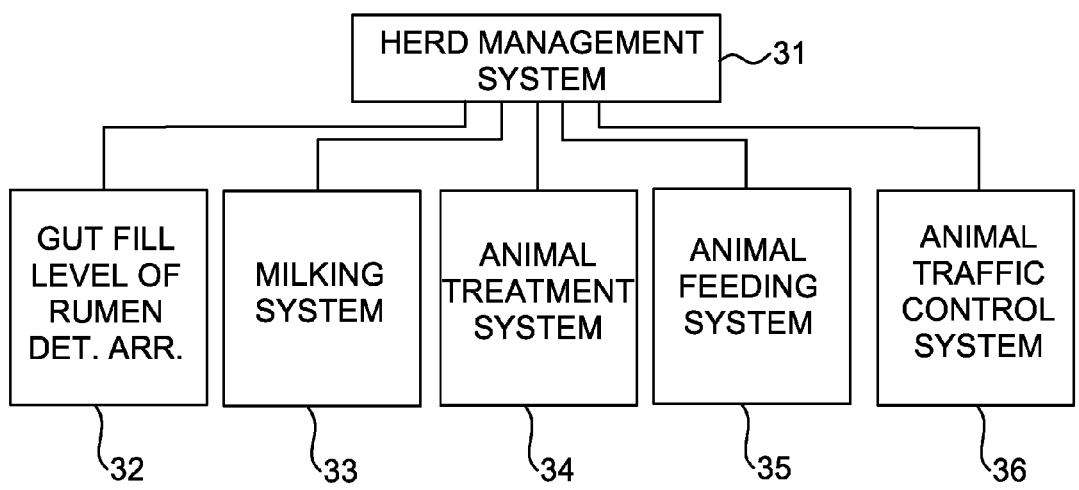
FIG. 3 illustrates schematically an animal arrangement including a herd management system according to an embodiment of the invention.

Further, the inventive arrangement may be operatively connected to a herd management system and deliver gut fill level data thereto as being illustrated in FIG. 3. Here, the herd management system is denoted by 31 whereas the inventive arrangement for determining gut fill levels is denoted by 32. The animal arrangement of FIG. 3 further includes a milking system 33, an animal treatment system 34, an animal feeding system 35, and an animal traffic control system 36, each being supervised and controlled by the herd management system 31 and each supplying the herd management system 31 with relevant data.

The gut fill levels could be tracked and compared with the expected gut fill levels at each instant e.g. by the herd management system 31. The expected gut fill levels could be historical gut fill levels values for that cow 10 or for a similar cow or group of cows (race, age, etc.), optionally compensated for the increasing age of the cow 10 or for other parameters such as e.g. lactation stage.

If the measured gut fill level of the rumen of a cow 10 deviates from the expected gut fill level by at least a given amount, this may trigger an alarm to be activated or an action to be taken automatically with respect to the cow 10, e.g. the cow 10 could be treated in some manner, by means of the animal treatment system 34 operatively connected to the herd management system 31, or the feeding of the cow 10 could be changed with respect e.g. to its nutritional content by the animal feeding system 35 operatively connected to the herd management system 31. For instance, the determination of the gut fill level of the rumen of a cow 10 can be used in identification of bloat, a lethal condition for cows. Particularly grazing cows are susceptible to bloat. Typically, if a cow is bloated, the rumen will bulging slightly and feel distended and tight like a balloon. If the herd management system 31 detects bloat the animal treatment system 34 will be alerted for treatment of the cow in question.

Generally, such alarm or other actions may also be triggered depending on the composition, particle size, structure, digestibility, and/or fiber content of feed last consumed by the cow 10, the time lapsed since feed was last consumed by the cow 10, and/or the amount of feed last consumed by the cow 10.

It shall here be stressed that the gut fill level of the rumen of a cow 10 is a result of dry matter intake, ration composition, digestion, and the passage rate of ingested food. The digestibility of a feed ration is the result of the feed retention time in the rumen and the degradation characteristics of ingested nutrients (particle sixe, type of fibers, etc.). The more fibers that are ingested, the lower is the digestibility and the longer is the passage rate. This has to be taken into consideration when determining whether an alarm should be triggered and/or whether any other action should be performed.

Further, the gut fill level may be used for determination of how much a cow 10 has been eating between two gut fill level determinations. Typically, a cow 10 that has been eating considerably has an extended or convex rumen triangle whereas a cow with an empty rumen has an intended, hollow, or concave rumen triangle. Thus, it can be determined if a cow has been eating sufficient dry matter during a particular period of time, i.e. if the cow is satisfied or is still hungry. If the cow has not received sufficient feed the herd management system 31 may alert the animal feeding system 35 to offer the cow 10 more or different feed, or may alert the animal traffic control system 36 to direct the cow 10 to a paddock with fresh grass. A low feed intake can also indicate illness in which case the cow should be given a medicament or a treatment.

On a group level, a sudden change of the gut fill levels may indicate that it is something wrong with the feed ration for this group, e.g. the feed composition and/or amount of feed. Accordingly, the herd management system 31 may alert the animal feeding system 35 to offer the cows in this group a different feed ration, i.e. more/less or different feed.

It shall be appreciated that the herd management system 31 may be arranged to automatically initiate any of the disclosed or other animal related actions with respect to a cow 10 also based on the stage of lactation of the cow 10.

During a first part of the lactation of a cow 10, the feed ration typically provides more energy via feed ingredients having higher digestibility and lower amount of fibers, whereas at the end of the lactation and during a first part of the transition period of dry cows the feed ration contains less energy and thus less digestible ingredients. Thus, the interpretation of the determined gut fill level is different depending on the stage of the lactation. For instance, early lactation cows are expected to have gut fill level of 3 (lower is not desired and may indicate to little feed intake and higher may indicate too high feed intake or bloat). Dry cows are expected to have gut fill levels of 4 or 5 as the feed passage rate is lower. A gut fill level below 4 would indicate too low feed intake or faster passage rate then expected.

Further, the gut fill levels should be cross-linked with other available parameters in the herd management system 31 to provide reliable data for triggering various activities. Thus, in one embodiment, the herd management system 31 is arranged to automatically initiate an animal related action also based on any of feed intake information such as feeding time and frequency and feed composition, milk performance information, ailment and/or treatment information, health information, veterinary visit information, hoof trimmer information, body condition score information, and activity information for that cow 10. A herd management parameter such as ketosis can be double-checked by cross-linking the data with the gut fill level(s).

Using the gut fill levels as a further input parameter into the herd management system, a strengthened monitoring and controlling concept is obtained. In particular, using gut fill levels for monitoring and controlling digestion and health of cows at around the calving period and early lactation is of high importance—both on cow individual and group levels. Gut fill levels are also valid information during the dry off phase and for heifers shortly before calving. It has been indicated that such cows having low gut fill levels some days before calving can be expected to have high body temperature (fever) more often with typical fresh cow ailments and more treatments.

Also long term effects can be expected. If a cow starts with low gut fill levels after calving (e.g. 1 or 2), it is likely that it stays with low gut fill levels and low feed intake for the next seven days. In such situation the risk for ketosis is increased and the herd management system 31 should give a warning or alarm also for this long term changes.

Monitoring of feed intake in young stock and in pregnant heifers can also be an important application. Feed ration composition and allocated feed amount need careful monitoring, as especially pregnant heifers have to use the allocated feed to grow the fetus but at the same time to still grow themselves. Low gut fill levels should be an indication to the herd manager to improve the feed—ether on group or on individual level.

Yet further, this information may be used also in the milking system 33. If the milking system 33 has a waiting area in front of the entrance to the milking area, a cow 10 that has been determined (via the gut fill level determinations) to not be hungry, may not be allowed to enter the waiting area even if the cow 10 otherwise has milking permission, since a cow that is not hungry may not be in any particular hurry to enter the milking area and pass through the milking system 33. Such cow may block the traffic pattern and it may be better to allow the cow 10 to wait further until the cow is admitted to enter the waiting area of the milking system 33.

For animal arrangements with paddocks, the inventive arrangement may be used for determining how much grass that has been consumed by a herd of cows during a period of time. If the cows have their gut fill levels determined at the time of entrance to the paddock and at the time of exit from the paddock, the consumption of the cows can be determined and the amount of grass consumed in the paddock is obtained. This aspect of the invention may be particularly useful as a means for determining grazing hours left within the invention disclosed in WO2012/004110, the contents of which being hereby incorporated by reference.

It shall be appreciated that the herd management system 31 may be arranged to communicate with the arrangement for determining a gut fill level of the rumen of a cow in both directions. Data for e.g. normalization purposes may be forwarded from the herd management system 31 to the arrangement for determining a gut fill level of the rumen of a cow. Also other data that can be used in the determination of the gut fill level may be forwarded from the herd management system 31.

It shall further be appreciated that the image processing system 12 may be integrated into the herd management system 31 especially if the animal arrangement handles a limited number of cows. In such an instance, the image data as measured is sent from the three-dimensional camera 11 to the herd management system 31 for further analysis.

While the invention has been described above by way of example, it shall be understood that the same may be varied in several details. In particular, the various features and embodiments disclosed above may be combined in a number of further ways readily available to a person skilled in the art to thereby form yet further embodiments of the invention. Further, embodiments of the invention may only comprise some of the features disclosed above with reference to a particular embodiment. The objects and advantages of the present invention as disclosed herein are accomplished and obtained by each of the embodiments of the invention. The scope of the present patent is defined by the following claims.

The invention claimed is:

1. A method for determining a gut fill level of a rumen of an animal having a rumen triangle defined by a paralumbar fossa of the animal, comprising the steps of:
   forcing the animal to stand essentially still within a station;
   with the animal standing essentially still in the station, and with a three-dimensional camera (11) located at a position on a left side of the animal, at a height above the rumen triangle of the animal, longitudinally in essence in level with the rumen triangle, and directed downward towards the rumen triangle, recording a three-dimensional image of at least a portion of the animal;
   automatically image analyzing the recorded three-dimensional image within an image processing system; and
   using the image processing system, automatically determining the gut fill level of the rumen of the animal based on the analyzed three-dimensional image,
   wherein the gut fill level of the rumen is automatically determined by the image processing system first automatically determining at least one of
   i) a depth of one of a) a convexity of the rumen triangle and b) a concavity of the rumen triangle, and
   ii) a volume of one of a) a convexity of the rumen triangle and b) a concavity of the rumen triangle, and
   second automatically determining the gut fill level of the rumen of the animal based on the determined at least one of the depth and the volume of the convexity or concavity of the rumen triangle.

2. The method of claim 1, wherein,
   the three-dimensional camera comprises optical axes, and when recording the three-dimensional image, the three-dimensional camera is
   i) located at the position on the left side of the animal longitudinally in essence in level with the rumen triangle so that the optical axes of the three-dimensional camera is perpendicular to a longitudinal axis of the animal within a deviation from a perpendicular direction to the longitudinal axis of the animal so that a bottom of the rumen triangle concavity is visible in the three-dimensional image, and
   ii) directed downwards towards the rumen triangle so that the bottom of the rumen triangle concavity is visible in the three-dimensional image.

3. The method of claim 1, wherein,
   the three-dimensional camera comprises optical axes, and when recording the three-dimensional image, the three-dimensional camera is
   i) located at the position on the left side of the animal longitudinally in essence in level with the rumen triangle so that the optical axes of the three-dimensional camera is perpendicular to a longitudinal axis of the animal within a deviation of 15 degrees from a perpendicular direction to the longitudinal axis of the animal, and ii) directed downwards almost tangentially towards the rumen triangle.

4. The method of claim 1, wherein,
the three-dimensional camera comprises optical axes, and when recording the three-dimensional image, the three-dimensional camera is
i) located at the position on the left side of the animal longitudinally in essence in level with the rumen triangle so that the optical axes of the three-dimensional camera is perpendicular to a longitudinal axis of the animal within a deviation of 15 degrees from a perpendicular direction to the longitudinal axis of the animal so that a bottom of the rumen triangle concavity is visible in the three-dimensional image, and
ii) directed downwards towards the rumen triangle with an angle, between optical axes of the three-dimensional camera and a horizontal plane, of between 25 and 75 degrees, with the bottom of the rumen triangle concavity visible in the three-dimensional image.

5. The method of claim 1, wherein,
wherein the gut fill level of the rumen is automatically determined by the image processing system
i) first automatically determining the depth of one of a) the convexity of the rumen triangle and b) the concavity of the rumen triangle, and
ii) second automatically determining the gut fill level of the rumen of the animal based on the determined depth of the convexity or concavity of the rumen triangle, and
the determined depth is a depth normalized with respect to a size of the animal.

6. The method of claim 1, wherein,
wherein the gut fill level of the rumen is automatically determined by the image processing system
i) first automatically determining the volume of one of a) the convexity of the rumen triangle and b) the concavity of the rumen triangle, and
ii) second automatically determining the gut fill level of the rumen of the animal based on the determined volume of the convexity or concavity of the rumen triangle, and
wherein the determined volume is a volume normalized with respect to a size of the animal.

7. The method of claim 5, wherein the size of the animal is given as at least one of the group consisting of a length of the animal, a height of the animal, a width of the animal, a volume of the animal, and a weight of the animal.

8. The method of claim 6, wherein the size of the animal is given as at least one of the group consisting of a length of the animal, a height of the animal, a width of the animal, a volume of the animal, and a weight of the animal.

9. The method of claim 1, comprising the further step of:
automatically calculating at least one of i) a previously determined depth and ii) a previous determined volume of the one of a) the convexity of the rumen triangle and b) the concavity of the rumen triangle based on a previous recording of another three-dimensional image of the at least a portion of the animal, and
wherein said step of automatically determining the gut fill level of the rumen is based a comparison of i) the determined at least one of the depth and the volume of the convexity or concavity of the rumen triangle to ii) the calculated at least one of i) the previously determined depth and ii) the previous determined volume of the one of a) the convexity of the rumen triangle and b) the concavity of the rumen triangle.

10. The method of claim 1, wherein said automatically determining step comprises providing results of the image analysis of the three-dimensional image to a model that links the results of the image analysis of the three-dimensional image to at least one of i) independently measured depths of convexity or concavity of the rumen triangle of animals, and ii) manually determined gut fill levels.

11. The method of claim 1, wherein,
said automatically determining step comprises analyzing a convexity of the rumen triangle from the three-dimensional image,
the analyzed convexity of the rumen triangle being used to determine the depth of the convexity of the rumen triangle, and
the determined depth of the of the convexity of rumen triangle being used to determine the gut fill level of the rumen.

12. The method of claim 1, wherein,
said automatically determining step comprises analyzing a concavity of the rumen triangle,
the analyzed concavity of the rumen triangle being used to determine the depth of the concavity of the rumen triangle, and
the determined depth of the concavity of the rumen triangle being used to determine the gut fill level of the rumen.

13. The method of claim 1, in combination with a method of animal handling, wherein the combination comprises the further steps of:
automatically forwarding the determined gut fill level to a herd management system; and
automatically initiating an animal related action based on the determined gut fill level.

14. A system for determining a gut fill level of a rumen of an animal (10) having a rumen triangle defined by a paralumbar fossa of the animal, the system comprising:
a three-dimensional camera (11) located, within a station where the animal is forced to stand essentially still, at a position on a left side of where the animal would stand, at a height above the rumen triangle of the animal, longitudinally in essence in level with the rumen triangle, and directed downward towards the rumen triangle, wherein the thus located and positioned three-dimensional camera records a three-dimensional image of at least a portion of the standing-still animal; and
an image processing device (12) operatively connected to the three-dimensional camera and that receives the recorded three-dimensional image from the three-dimensional camera,
wherein the image process device (12) automatically analyzes the three-dimensional image and determines the gut fill level of the rumen of the animal based on the analyzed three-dimensional image, the gut fill level of the rumen being automatically determined by the image processing system first automatically determining at least one of
i) a depth of one of a) a convexity of the rumen triangle and b) a concavity of the rumen triangle, and
ii) a volume of one of a) a convexity of the rumen triangle and b) a concavity of the rumen triangle, and
second automatically determining the gut fill level of the rumen of the animal based on the determined at least one of the depth and the volume of the convexity or concavity of the rumen triangle.

15. The system of claim 14, in combination with a herd management system (31), wherein, the herd management system is operatively connected to the image process device (12) and is automatically supplied with the determined gut fill level of the rumen of the animal, and the herd management system automatically initiates an animal related action based on the determined gut fill level.

16. The system of claim 14, wherein, the three-dimensional camera comprises optical axes, and the three-dimensional camera is i) located at the position on the left side of the animal longitudinally in essence in level with the rumen triangle so that the optical axes of the three-dimensional camera is perpendicular to a longitudinal axis of the animal within a deviation of 15 degrees from a perpendicular direction to the longitudinal axis of the animal so that a bottom of the rumen triangle concavity is visible in the three-dimensional image, and ii) directed downwards towards the rumen triangle with an angle, between optical axes of the three-dimensional camera and a horizontal plane, of between 25 and 75 degrees so that the bottom of the rumen triangle concavity is visible in the three-dimensional image.

17. The system of claim 14, wherein, image process device (12) automatically determines the gut fill level of the rumen by i) first automatically determining the depth of one of a) the convexity of the rumen triangle and b) the concavity of the rumen triangle, and ii) second automatically determining the gut fill level of the rumen of the animal based on the determined depth of the convexity or concavity of the rumen triangle, and the determined depth is a depth normalized with respect to a size of the animal.

18. The system of claim 14, wherein, image process device (12) automatically determines the gut fill level of the rumen by i) first automatically determining the volume of one of a) the convexity of the rumen triangle and b) the concavity of the rumen triangle, and ii) second automatically determining the gut fill level of the rumen of the animal based on the determined volume of the convexity or concavity of the rumen triangle, and wherein the determined volume is a volume normalized with respect to a size of the animal.

19. The system of claim 14, automatically calculating at least one of i) a previously determined depth and ii) a previous determined volume of the one of a) the convexity of the rumen triangle and b) the concavity of the rumen triangle based on a previous recording of another three-dimensional image of the at least a portion of the animal, and wherein said step of automatically determining the gut fill level of the rumen is based a comparison of i) the determined at least one of the depth and the volume of the convexity or concavity of the rumen triangle to ii) the calculated at least one of i) the previously determined depth and ii) the previous determined volume of the one of a) the convexity of the rumen triangle and b) the concavity of the rumen triangle.

20. A method for determining a gut fill level of a rumen of an animal having a rumen triangle defined by a paralumbar fossa of the animal, comprising the steps of:

with the animal standing still, and with a three-dimensional camera (11) located at a position on a left side of the animal, at a height above the rumen triangle of the animal, longitudinally in essence in level with the rumen triangle, and directed downward towards the rumen triangle so that a bottom of the rumen triangle concavity is visible in the three-dimensional camera, recording a three-dimensional image of at least a portion of the animal so that the bottom of the rumen triangle concavity is visible in the three-dimensional image;

automatically image analyzing the recorded three-dimensional image within an image processing system; and using the image processing system, automatically determining the gut fill level of the rumen of the animal based on the analyzed three-dimensional image, wherein the gut fill level of the rumen is automatically determined by the image processing system first automatically determining at least one of i) a depth of one of a) a convexity of the rumen triangle and b) a concavity of the rumen triangle through, and ii) a volume of one of a) a convexity of the rumen triangle and b) a concavity of the rumen triangle, and second automatically determining the gut fill level of the rumen of the animal based on the determined at least one of the depth and the volume of the convexity or concavity of the rumen triangle.

* * * * *